United States Patent
Pineau (10) Patent No.: US 10,323,130 B2
(45) Date of Patent: Jun. 18, 2019

(54) WATER-DISPERSIBLE POLYAMIDE POWDER

(71) Applicant: ARKEMA FRANCE, Colombes (FR)

(72) Inventor: Quentin Pineau, Evreux (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 14/413,114

(22) PCT Filed: Jul. 8, 2013

(86) PCT No.: PCT/FR2013/051624
§ 371 (c)(1),
(2) Date: Jan. 6, 2015

(87) PCT Pub. No.: WO2014/006353
PCT Pub. Date: Jan. 9, 2014

(65) Prior Publication Data
US 2015/0166736 A1  Jun. 18, 2015

(30) Foreign Application Priority Data

Jul. 6, 2012 (FR) .................................. 12 56546

(51) Int. Cl.
*C08J 3/12* (2006.01)
*C08L 77/06* (2006.01)
(Continued)

(52) U.S. Cl.
CPC ............. *C08J 3/12* (2013.01); *A61K 8/022* (2013.01); *A61K 8/0279* (2013.01); *A61K 8/88* (2013.01);
(Continued)

(58) Field of Classification Search
CPC ............................................ Y10T 428/2982
See application file for complete search history.

(56) References Cited

U.S. PATENT DOCUMENTS

| 5,804,682 A | 9/1998 | Fischer et al. |
| 2003/0114636 A1* | 6/2003 | Schiffer .......... A61K 8/365 528/310 |

(Continued)

FOREIGN PATENT DOCUMENTS

| EP | 0 062 138 A1 | 10/1982 |
| WO | WO 97/47686 A1 | 12/1997 |

(Continued)

OTHER PUBLICATIONS

International Search Report (PCT/ISA/210) dated Sep. 4, 2013, by the French Patent Office as the International Searching Authority for International Application No. PCT/FR2013/051624.

Primary Examiner — Bethany P Barham
Assistant Examiner — Dominic Lazaro
(74) Attorney, Agent, or Firm — Buchanan Ingersoll & Rooney P.C.

(57) ABSTRACT

A powder of polyamide particles, in which: said polyamide includes more than 50 mol % of amine ends among the total number of amine and acid ends of the polyamide; said particles include, on the surface thereof, primary amine groups neutralized by a phosphorous Bronsted acid, such as phosphoric acid; and the D50 of the particles falls within the range of 100 nm to 50 μm, preferably 100 nm to 20 μm. A method for producing such a powder and to the production of aqueous dispersions including same.

15 Claims, 2 Drawing Sheets

(51) Int. Cl.
    *C08G 69/48* (2006.01)
    *A61Q 19/00* (2006.01)
    *A61K 8/88* (2006.01)
    *C08G 69/26* (2006.01)
    *C08G 69/36* (2006.01)
    *C08L 77/00* (2006.01)
    *A61K 8/02* (2006.01)
    *C08J 3/16* (2006.01)

(52) U.S. Cl.
    CPC ............ *A61Q 19/00* (2013.01); *C08G 69/26* (2013.01); *C08G 69/36* (2013.01); *C08G 69/48* (2013.01); *C08J 3/16* (2013.01); *C08L 77/00* (2013.01); *C08L 77/06* (2013.01); *A61K 2800/412* (2013.01); *C08J 2377/00* (2013.01); *C08J 2377/06* (2013.01); *C08L 2201/54* (2013.01); *Y10T 428/2982* (2015.01)

(56) References Cited

U.S. PATENT DOCUMENTS

2009/0061227 A1\* 3/2009 Asano ................ C08J 3/14
            428/402
2013/0142747 A1\* 6/2013 Pineau ............... A61K 8/88
            424/70.7

FOREIGN PATENT DOCUMENTS

| WO | WO 98/44062 A1 | 10/1998 | |
|---|---|---|---|
| WO | WO2006/037665 | \* 4/2006 | |
| WO | WO 2012/001299 A1 | 1/2012 | |
| WO | WO-2012001299 A1 \* | 1/2012 | ............... A61K 8/88 |

\* cited by examiner

Figure 1

Figure 2

WATER-DISPERSIBLE POLYAMIDE POWDER

FIELD OF THE INVENTION

The present invention relates to water-dispersible polyamide powder, and in particular the manufacture of stable aqueous dispersions of fine polyamide particles.

"Stable dispersion" means, in the sense of the invention, a dispersion that does not undergo flocculation, the polyamide particles of which do not form aggregates, even after 24 months at a temperature of 20° C. However, the powder particles of the stable dispersion may undergo sedimentation, but are capable of redispersing spontaneously by simple stirring at room temperature.

"Water-dispersible" means a polyamide powder which, when introduced into water at 20° C., at a concentration by weight in the range from 0.5 to 90%, allows a macroscopically homogeneous solution to be obtained.

"Fine particles" means particles with a median diameter by volume (hereinafter D50) less than or equal to 50 μm.

In the sense of the invention, "D50" corresponds to the average size by volume, i.e. the value of the particle size that divides the population of particles examined exactly into two. D50 is measured according to standard ISO 9276— parts 1 to 6: "Representation of data obtained by granulometric analysis".

PRIOR ART

Aqueous polyamide dispersions are widely used in inks, coating films, textile treatments, fabric covering, treatment of paper, paints, lubricants, hot melt adhesives (HMA). These aqueous dispersions are difficult to obtain starting from the commercially available polyamides, intended for industrial use, which are generally in the form of powders or granules. The existing polyamide powders are not, as such, dispersible directly in an aqueous medium, and therefore cannot form a stable homogeneous aqueous dispersion.

In fact, the known methods for manufacture of aqueous polyamide dispersions generally require numerous steps, are very complex technically, and are costly in terms of energy. In these methods, the polyamide is melted and then dispersed in an aqueous medium using organic solvent(s) and/or dispersant(s) by various methods, described for example in patent documents WO9747686 or WO9844062. In particular, polyamides of high molecular weight require large amounts of organic solvent, and form extremely viscous solutions that are difficult to disperse in aqueous media.

Moreover, it is not possible to prepare a dispersion of polyamide in an aqueous medium by a direct process of emulsion polymerization owing to the method of manufacture of the polyamide, typically by polycondensation or by ring opening. The current methods are therefore based either on reprecipitation, or on post-emulsification. Reprecipitation consists of dissolving the polyamide in an organic solvent, reprecipitating the polyamide in the form of particles and then replacing the organic solvent with an aqueous medium. However, the size of the particles thus obtained is too large (D50 greater than 50 μm) to give a stable dispersion, which is an obstacle to the use of such dispersions in inks and paints. In fact, in these dispersions, the particles have a tendency to aggregate, or even flocculate, in the aqueous medium, so that the aqueous dispersion is not stable. Finally, inclusion of the additional step of replacement of the organic solvent with an aqueous medium complicates the conventional process of reprecipitation for manufacturing polyamide powder. In post-emulsification, the polyamide is first dissolved in an organic solvent so as to prepare a solution, then the polyamide solution is mixed with an emulsifier in an aqueous medium, and emulsified using strong shearing to form an aqueous dispersion of polyamide. However, polyamide is only slightly soluble in organic solvents, so that the post-emulsification method is not economically viable, as its productivity is too low. Moreover, the post-emulsification method uses large amounts of organic solvents, which are factors in environmental pollution. Finally, an aqueous dispersion of polyamide obtained by post-emulsification inevitably contains residues of organic solvents and emulsifiers.

The existing techniques do not allow stable aqueous dispersions to be obtained at high concentration of polyamide, notably if the concentration of polyamide exceeds 50 wt % in the aqueous medium.

To be usable in the field of inks and paints, the polyamide particles in the aqueous dispersion must be very fine, with D50 less than or equal to 50 μm. Aqueous dispersions of polyamides commonly used in inks, binders and adhesives are those that contain fine particles of copolyamides based on dimers of fatty acids. The method for obtaining these, described notably in the Henkel patent document (U.S. Pat. No. 5,804,682), requires dissolving the copolyamide (hereinafter COPA) based on fatty acid dimer in a "light" alcohol (of the isobutanol type) before adding water, a surfactant, and thickeners to form an emulsion, then evaporating the alcohol to recover an aqueous dispersion of COPA based on fatty acid dimer. These aqueous dispersions of COPA based on fatty acid dimer must contain a surfactant based on toxic and carcinogenic nonylphenol in order to remain stable. Compared to the other copolyamides, the copolyamides based on dimers of fatty acids have the particular features of being much less crystalline, with low chemical resistance (with respect to solvents) and of low modulus, and they are very tackifying, which lowers the productivity of processes that use dispersions of this kind. The COPA dimers of fatty acids are soluble in C1 to C6 light alcohols with a single alcohol function and low boiling point (boiling point below 120° C.). However, the COPAs other than fatty acid dimers are insoluble in light alcohols of this type with a single alcohol function, such as isobutanol. Therefore this process, notably described in U.S. Pat. No. 5,804,682, is not feasible for the vast majority of the polyamides that are more crystalline than these COPA dimers of fatty acids.

There is therefore a real need to supply aqueous dispersions using all types of polyamides, including polyamides other than the copolyamides based on dimers of fatty acids.

For example, certain copolyamides are familiar as adhesives of the "hot melt adhesive" (or HMA) type, i.e. they are deposited in the molten state on the surfaces to be glued, adhesion then being obtained by cooling, on return of the copolyamides to the solid state. The melting point of these COPA HMAs is generally in the range from 80 to 190° C., preferably from 100 to 130° C. The composition of monomers and the weight ratio between the monomers notably determine the properties of adherence on different supports and the chemical resistance of these COPAs. These properties of the COPA HMAs are already exploited in the textile industry, in the manufacture of films, filaments, voiles or screens, varnish, paints, inks and the coating of materials, notably in the form of fine powders of COPA. However, these powders are not water-dispersible. Moreover, using atmospheric grinding, or even cryogenic grinding at a temperature below Tg (glass transition temperature of the polymer), generally at −100° C., it proves very difficult to obtain powders of COPA HMA with D50 below 60 μm. In fact, the methods used are very expensive and have very low productivity, involve high losses, require several recyclings and passes in the grinding mill, are very time-consuming and energy-consuming, and in addition require selecting the powder by sieving. This is associated with the fact that the HMAs have a tendency to become elastic and to heat up, which makes grinding of them particularly difficult.

Therefore the aim of the present invention is to supply a method for manufacturing water-dispersible PA powders, and aqueous polyamide dispersions, notably of COPA, such as the COPA HMAs, ready for use, which facilitate use of them by the formulators, by being directly usable (by simple incorporation) in formulations.

The present invention notably has the aim of supplying a simple method (comprising as few steps as possible) for manufacturing said polyamide powders ready for use, starting from a polyamide regardless of its form: granules, powder, liquid (molten) or solid, etc.

Surprisingly, the applicant has shown that the addition of a phosphorus-based Brønsted acid (abbreviated hereinafter to "acid P"), such as phosphoric acid, to a mixture of polyamide and water, makes it possible, in certain conditions specific to the invention, to prepare stable aqueous polyamide dispersions and even obtain an atypical morphology of fine powder of polyamide, having the particular feature of being water-dispersible.

DETAILED DESCRIPTION OF THE INVENTION

In the present description, it should be noted that when referring to ranges, expressions of the type "in the range from . . . to . . . " or "containing/comprising from . . . to . . . " include the limits of the range. Conversely, expressions of the type "between . . . and . . . " exclude the limits of the range.

The present invention therefore relates to a powder based on polyamide particles in which:
said polyamide comprises more than 50 mol % of amine ends among the total number of amine and acid ends of the polyamide;
said particles bear, on their surface, primary amine groups at least partially neutralized by a phosphorus-based Brønsted acid ("acid P"), preferably phosphoric acid;
the D50 of the particles is in the range from 100 nm to 50 µm, preferably from 100 nm to 20 µm.

"Phosphorus-based Brønsted acid" means any acid comprising phosphorus and able to give up a proton i.e. an H+ ion in an aqueous medium. The phosphorus-based Brønsted acid notably comprises at least one of the following acids: hypophosphorous acid $H_3PO_2$, phosphorous acid $H_3PO_3$, phosphoric acid $H_3PO_4$, perphosphoric acid $H_3PO_5$ and their derivatives such as sodium hypophosphite $NaH_2PO_2$, potassium hypophosphite $KH_2PO_2$, and mixtures thereof. Preferably, the phosphorus-based Brønsted acid comprises phosphoric acid, and more preferably consists of phosphoric acid $H_3PO_4$.

Advantageously, said polyamide powder according to the invention comprises at least one homopolyamide and/or at least one copolyamide (COPA).

Advantageously, said polyamide powder comprises at least one monomer selected from the aminocarboxylic, preferably alpha,omega-aminocarboxylic acids, comprising from 4 to 18 carbon atoms, the diamine-diacid couples comprising from 4 to 36 carbon atoms, the lactams comprising from 3 to 18 carbon atoms, and mixtures thereof.

According to a preferred embodiment of the invention, said particles based on polyamide comprise at least one polyamide and/or at least one copolyamide and/or mixtures thereof.

Polyamide (homopolyamide or copolyamide) in the sense of the invention means the products of condensation of the lactams, amino acids and/or diacids with diamines and, as a general rule, any polymer formed by units or monomers joined together by amide groups.

The term "monomer" in the present description of the powders of polyamides must be understood in the sense of "repeating unit". A particular case is when a repeating unit of the polyamide consists of the association of a diacid with a diamine. It is considered that it is the association of a diamine and a diacid, i.e. the diamine-diacid couple (in equimolar amount), that corresponds to the monomer. This is explained by the fact that individually, the diacid or the diamine is only one structural unit, which on its own is insufficient to polymerize. In the case when the powder particles according to the invention comprise at least two different monomers, called "co-monomers", i.e. at least one monomer and at least one co-monomer (monomer different from the first monomer), they comprise a copolymer such as a copolyamide, abbreviated to COPA.

Copolyamide (abbreviated to COPA) means the products of polymerization of at least two different monomers selected from:
monomers of the amino acid or aminocarboxylic acid type, and preferably alpha,omega-aminocarboxylic acids;
monomers of the lactam type having from 3 to 18 carbon atoms on the main ring, and possibly substituted;
monomers of the "diamine-diacid" type resulting from reaction between an aliphatic diamine having from 4 to 36 carbon atoms, preferably from 4 to 18 carbon atoms and a dicarboxylic acid having from 4 to 36 carbon atoms, preferably from 4 to 18 carbon atoms; and
mixtures thereof with monomers with a different number of carbons in the case of mixtures between a monomer of the amino acid type and a monomer of the lactam type.

Monomers of the Amino Acid Type:
As examples of alpha,omega-amino acids, we may mention those having from 4 to 18 carbon atoms, such as the aminocaproic, 7-aminoheptanoic, 11-aminoundecanoic, N-heptyl-11-aminoundecanoic and 12-aminododecanoic acids.

Monomers of the Lactam Type:
As examples of lactams, we may mention those having from 3 to 18 carbon atoms on the main ring, and possibly substituted. We may mention for example β,β-dimethylpropiolactam, α,α-dimethylpropiolactam, amylolactam, caprolactam also called lactam 6, capryllactam also called lactam 8, oenantholactam and lauryllactam also called lactam 12.

Monomers of the "Diamine-Diacid" Type:
As examples of dicarboxylic acid, we may mention the acids having from 4 to 36 carbon atoms. We may mention for example, adipic acid, sebacic acid, azelaic acid, suberic acid, isophthalic acid, butanedioic acid, 1,4-cyclohexyldicarboxylic acid, terephthalic acid, sodium salt or lithium salt of sulfoisophthalic acid, the dimerized fatty acids (these dimerized fatty acids have a dimer content of at least 98% and are preferably hydrogenated) and dodecanedioic acid $HOOC-(CH_2)_{10}-COOH$, and tetradecanedioic acid.

More particularly, fatty acid dimers or dimerized fatty acids mean the product of the dimerization reaction of fatty acids (generally containing 18 carbon atoms, often a mixture of oleic and/or linoleic acid). It is preferably a mixture comprising from 0 to 15% of C18 monoacids, from 60 to 99% of C36 diacids, and from 0.2 to 35% of triacids or polyacids with C54 or more.

As examples of diamine, we may mention the aliphatic diamines having from 4 to 36 atoms, preferably from 4 to 18 atoms, which may be arylic and/or saturated cyclic. As examples we may mention hexamethylenediamine, piperazine (abbreviated to "Pip"), aminoethylenepiperazine, tetramethylenediamine, octamethylenediamine, decamethylenediamine, dodecamethylenediamine, 1,5-diaminohexane, 2,2,4-trimethyl-1,6-diaminohexane, the diamine polyols, isophorone diamine (IPD), methyl pentamethylenediamine (MPMD), bis(aminocyclohexyl)methane (BACM), bis(3-methyl-4 aminocyclohexyl)methane (BMACM), meta-xylylenediamine, and bis-p aminocyclohexylmethane.

As examples of monomers of the "diamine-diacid" type, we may mention those resulting from the condensation of hexamethylenediamine with a C6 to C36 diacid, notably the monomers: 6.6, 6.10, 6.11, 6.12, 6.14, 6.18. We may mention the monomers resulting from the condensation of decanediamine with a C6 to C36 diacid, notably the monomers: 10.10, 10.12, 10.14, 10.18.

Preferably, the polyamide powders of the invention comprise at least one polyamide selected from the polyamides and copolyamides comprising at least one of the following monomers: 4.6, 4.T, 5.6, 5.9, 5.10, 5.12, 5.13, 5.14, 5.16, 5.18, 5.36, 6, 6.6, 6.9, 6.10, 6.12, 6.13, 6.14, 6.16, 6.18, 6.36, 6.T, 9, 10.6, 10.9, 10.10, 10.12, 10.13, 10.14, 10.16, 10.18, 10.36, 10.T, 11, 12, 12.6, 12.9, 12.10, 12.12, 12.13, 12.14, 12.16, 12.18, 12.36, 12.T, and mixtures thereof; in particular selected from PA 11, PA 12, PA 10.10, PA 6, PA 6.10, PA 10.12, PA 6.14 and/or PA 6.6/6, PA 6/12, PA 11/10.10, and mixtures thereof.

As examples of copolyamides formed from the various types of monomers described above, we may mention the copolyamides resulting from the condensation of at least two alpha,omega-aminocarboxylic acids or of two lactams or of one lactam and one alpha,omega-aminocarboxylic acid. We may, moreover, mention the copolyamides resulting from the condensation of at least one alpha,omega-aminocarboxylic acid (or one lactam), at least one diamine and at least one dicarboxylic acid. We may, moreover, mention the copolyamides resulting from the condensation of an aliphatic diamine with an aliphatic dicarboxylic acid and at least one other monomer selected from the aliphatic diamines different from the foregoing and the aliphatic diacids different from the foregoing.

As examples of copolyamides, we may mention copolymers of caprolactam and of lauryllactam (PA 6/12), copolymers of caprolactam, of hexamethylenediamine and of adipic acid (PA 6/6.6), copolymers of caprolactam, of lauryllactam, of hexamethylenediamine and of adipic acid (PA 6/12/6.6), copolymers of caprolactam, of hexamethylenediamine and of azelaic acid, of 11-aminoundecanoic acid, and of lauryllactam, (PA 6/6.9/11/12), copolymers of caprolactam, of adipic acid and of hexamethylenediamine, of 11-aminoundecanoic acid, of lauryllactam (PA 6/6.6/11/12), copolymers of hexamethylenediamine, of azelaic acid, and of lauryllactam (PA 6.9/12), copolymers of caprolactam and of 11-aminoundecanoic acid (PA 6/11), copolymers of lauryllactam and of capryllactam (PA 12/8), copolymers of capryllactam and of caprolactam (PA 8/6), copolymers of lauryllactam and of capryllactam (PA 12/8), copolymers of lauryllactam and of 11-aminoundecanoic acid (PA 12/11).

Advantageously, the COPA used in the composition according to the invention is obtained at least partially from biosourced raw materials.

The terms raw materials of renewable origin or biosourced raw materials mean materials that comprise biosourced carbon or carbon of renewable origin. In fact, in contrast to materials derived from fossil material, the materials consisting of renewable raw materials contain $^{14}C$. The "content of carbon of renewable origin" or "biosourced carbon content" is determined applying standards ASTM D 6866 (ASTM D 6866-06) and ASTM D 7026 (ASTM D 7026-04). As an example, COPAs based on polyamide 11 are derived at least partly from biosourced raw materials and have a biosourced carbon content of at least 1%, which corresponds to a $^{12}C/^{14}C$ isotope ratio of at least $1.2 \times 10^{-14}$. Preferably, the COPAs according to the invention comprise at least 50 wt % of biosourced carbon relative to the total weight of carbon, which corresponds to a $^{12}C/^{14}C$ isotope ratio of at least $0.6 \times 10^{-12}$. This content is advantageously higher, notably up to 100%, which corresponds to a C isotope ratio of $1.2 \times 10^{-12}$, in the case of COPAs derived entirely from raw materials of renewable origin.

As examples of amino acids of renewable origin, we may mention: 11-aminoundecanoic acid produced from castor oil for example, 12-aminododecanoic acid produced from castor oil for example, 10-aminodecanoic acid produced from decylenic acid obtained by metathesis of oleic acid for example, 9-aminononanoic acid produced from oleic acid for example.

As examples of diacids of renewable origin, we may mention, as a function of the number x of carbons in the molecule (Cx):
  C4: succinic acid from glucose for example;
  C6: adipic acid from glucose for example;
  C7: heptanedioic acid from castor oil;
  C9: azelaic acid from oleic acid (ozonolysis) for example;
  C10: sebacic acid from castor oil for example;
  C11: undecanedioic acid from castor oil;
  C12: dodecanedioic acid from biofermentation of dodecanoic acid=lauric acid (rich oil: cabbage palm oil and coconut oil) for example;
  C13: brassylic acid from erucic acid (ozonolysis) that occurs in colza for example;
  C14: tetradecanedioic acid by biofermentation of myristic acid (rich oil: cabbage palm oil and coconut oil) for example;
  C16: hexadecanedioic acid by biofermentation of palmitic acid (mainly palm oil) for example;
  C18: octadecanedioic acid obtained by biofermentation of stearic acid (a little in all vegetable oils but predominantly in animal fats) for example;
  C20: eicosanedioic acid obtained by biofermentation of arachidic acid (predominantly in colza oil) for example;
  C22: docosanedioic acid obtained by metathesis of undecylenic acid (castor oil) for example
  C36: fatty acid dimer obtained from the byproducts of resinous substances transformed by the Kraft process.

As examples of diamines of renewable origin, we may mention, as a function of the number x of carbons in the molecule (Cx):
  C4: butanediamine obtained by amination of succinic acid;
  C5: pentamethylenediamine (from lysine);
  and so on for the diamines obtained by amination of the diacids of renewable origin mentioned above.

Copolyamide of completely renewable origin means the copolyamides resulting from the polymerization of various monomers (renewable, nonrenewable or mixed) such as those mentioned above. This is so for example in the case of COPA 6.6/10.10 in which the "6.6" monomer is of nonrenewable origin whereas the "10.10" monomer is of renewable origin.

Copolyamide of completely renewable origin included in the composition according to the invention means the copolyamides resulting from the polymerization of various monomers, such as those mentioned above, for example the following copolyamides: PA 11/10.10, PA 11/10.36, PA 10.10/10.36, 11-aminoundecanoic/N-heptyl-11-aminoundecanoic copolyamide, etc.

Advantageously, one or more of the following copolyamides are used in the composition or the method of the present invention:

PA 6/6.6/12, for which the weight ratios of corresponding monomers may be (in percentages): 40/20/40, 35/20/45, 45/35/20, 30/30/40, 22/18/60, 40/25/35;
PA 6/6.6/11/12, for which the weight ratios of corresponding monomers may be for example (in percentages): 30/15/10/45, 30/20/20/30, or 15/25/25/35;
PA 6/12 of weight ratio 70/30;
PA 6.9/12 of weight ratio 30/70;
PA Pip.9/Pip.12/11 of weight ratio 15/70/15;
PA 6/IPD.6/12 of weight ratio 20/15/65;
PA IPD.9/12 of weight ratio 20/80;
PA6/MPMD.12/12 of weight ratio 27/33/33;
PA 6/6.12/12 of weight ratio 30/30/40;
PA 6/Pip.12/12 of weight ratio 30/20/50;
PA 6/6.12/11/PEG.12 of weight ratio 25/21/25/30;
PA 6.10/11/PEG.10 of weight ratio 14/14/42/30;
PA 6/6.6/6.10/6.1 of weight ratio 40/10/40/10;
PA 6.10/Pip.10/Pip.12 of weight ratio 20/40/40;
PA 6/11/12 of weight ratio 10/36/54;
PA Pip.12/12 of weight ratio 35/65;
PA IPD.10/12 of weight ratio 80/20;
PA Pip.10/12 of weight ratio 72/28;
PA 6/11 of weight ratio 50/50;
PA Pip.10/11/Pip.9 of weight ratio 65/30/5;
PA 6/6.6/6.10 of weight ratio 35/30/35

As examples of copolyamides, we may notably mention those marketed under the name Platamid® and Platamid® Rnew by ARKEMA, Vestamelt® by Evonik, and Griltex® by EMS.

Preferably the polyamide used in the present invention comprises at least one copolyamide selected from: PA 6/6.6/12, PA 6/6.6/11/12, PA 6/12, PA 6.9/12, PA Pip.9/Pip.12/11, PA 6/IPD.6/12, PA IPD.9/12, PA6/MPMD.12/12, PA 6/6.12/12, PA 6/Pip.12/12, PA 6/6.6/6.10/6.1, PA 6.10/Pip.10/Pip.12, PA 6/11/12, PA Pip.12/12, PA IPD.10/12, PA Pip.10/12, PA 6/11, PA Pip.10/11/Pip.9, PA 6/6.6/6.10, and in particular those with the weight ratios defined above, and mixtures of these copolyamides.

The ends or chain ends of these polyamides according to the invention are predominantly amine ends. It is possible to adapt the ends of the polyamides by using polyfunctional compounds and chain limiters, generally monofunctional compounds, during their synthesis.

Polyfunctional compound means a compound having more than 2 acid and/or amine functions. We may mention as examples diethylene triamine (DETA); a polyethertriamine, such as Jeffamine T403; bis(hexamethylene)triamine; EDTA; mellitic acid.

Chain limiting compound means a mono functional compound having 1 acid or amine reactive function, such as acetic acid, lauric acid, stearic acid, undecylenic acid, laurylamine.

Monoamine and/or diamine compounds are preferably used, to obtain (co)polyamides according to the invention that possess predominantly amine chain ends. In particular, during synthesis of these (co)polyamides that are used in the present invention, the condensation reactions take place with excess of amine functions.

Figure 1:
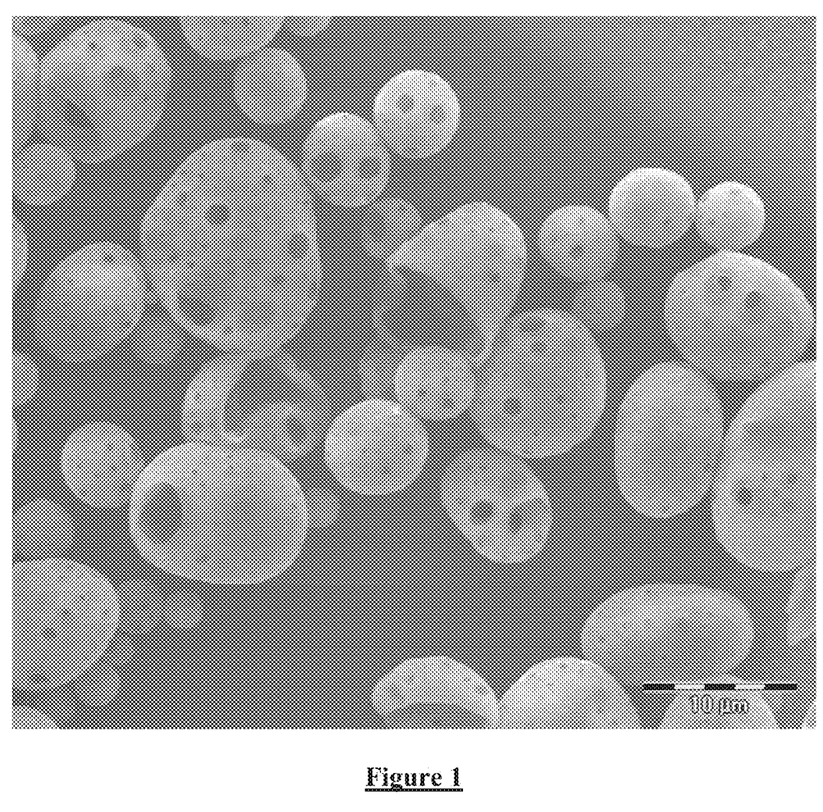
Figure 2:
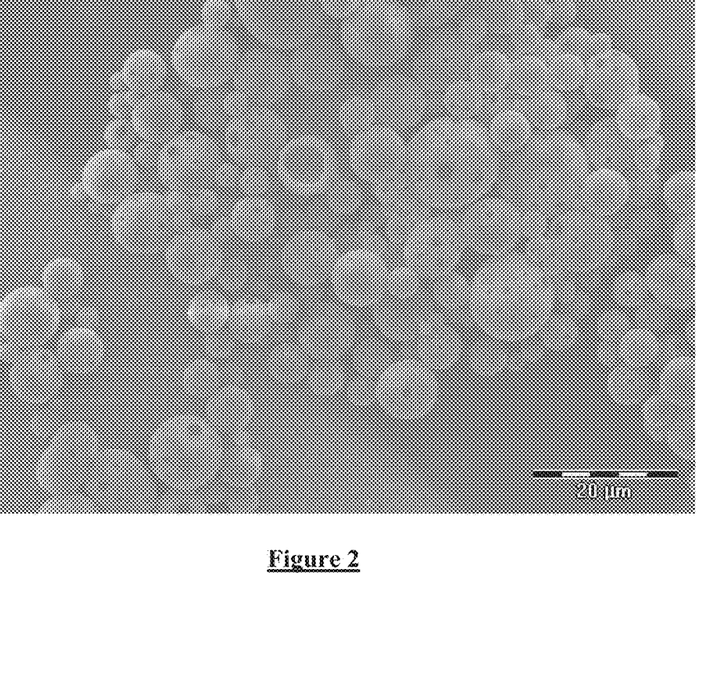

Advantageously, the polyamide powder of the invention comprises particles that are simultaneously:
of spheroidal shape,
with a surface or particle wall that is perforated or porous, and preferably hollow, i.e. the core (or central part) of the particles is empty, like those shown in the photographs in FIG. 1 and FIG. 2, observed with the scanning electron microscope, on the Philips XL30FEG SEM apparatus.

Preferably, the powder according to the invention contains at least 5%, preferably at least 15%, preferably at least 30%, preferably at least 50%, or even at least 70%, or better still at least 90 wt % of hollow particles, relative to the total weight of particles. Advantageously, the core of the particles of the invention contains at least one cosmetic, pharmaceutical or perfumery product. This special hollow morphology of the powders according to the invention allows them to be impregnated with these products not only on the surface but to a depth, even to the core of the particle, and to contain a larger amount of products than the powders of the prior art that are only porous at the surface.

In the present description, the granulometry of the powders is measured by laser diffraction, on Coulter® LS230 apparatus, according to standard ISO 9276.

Regarding the chemical characteristics of the powders, the percentage of amine ends is measured by potentiometric assay (acid-base), preferably with perchloric acid.

It is confirmed that the primary amine groups on the surface of the particles of a polyamide powder are at least partially neutralized, notably by a phosphorus-based Brønsted acid such as phosphoric acid, if the polyamide powder disperses in water at room temperature to form a milky liquid by simple stirring. Otherwise, notably if the powder does not form a liquid of milky appearance with water on stirring, and it settles to the bottom of the container despite stirring, the primary amine groups on the surface of the powders are not at least partially neutralized.

The physicochemical properties of the powder according to the invention mean that it is dispersible in an aqueous medium with neutral or acid pH, such as water, said medium having a pH in the range from 1 to 7, preferably from 4 to 6.5, to form a homogeneous composition or stable dispersion.

Aqueous medium with neutral or acid pH means, in the sense of the invention, any liquid medium comprising at least 50% of water, preferably at least 70% of water, preferably at least 80% of water, preferably at least 90% of water, preferably 100% of water, and with pH in the range from 1 to 7, preferably from 4 to 6.5. The water may be softened water, deionized water, distilled water, demineralized water and/or sterilized water, depending on its degree of purification, thermal water, etc.

The aqueous medium may further comprise water-miscible alcohols, preferably in which the number of carbons of the carbon chain does not exceed 6, such as ethanol or isopropanol. Alcoholic solutions obtained by simple mixing of these alcohols with water are also usable in the aqueous medium; as well as glycols, such as ethylene glycol, propylene glycol; polyols, such as glycerol or glycerin, sorbitol, sorbitol syrup.

Polyoxyethylene glycols (PEGs) may also be used as solvents in said aqueous medium. Carboxyvinyl polymers (carbomers or Carbopol), cyanoacrylic polymers; carbohydrate compounds, such as polysaccharides extracted from algae (alginates, carrageenans), from wood (cellulose and derivatives thereof), from the sap of trees (gum arabic, tragacanth), from seeds or pips (pectin, guar gum, carob gum, starch), from leaves (aloe gel); glycoproteins or proteoglycans; carbohydrate esters and ethers, may also be included in the composition of the aqueous medium, notably as thickeners or gelling agents of the aqueous medium.

Advantageously, preservatives, hydrophilic emulsifiers, colorants, humectants, gelling agents, hydrophilic active ingredients and any other hydrophilic cosmetic agent, may be included in the composition of said aqueous medium.

The present invention notably relates to a homogeneous fluid composition comprising:
from 0.5 to 90 wt % of powder as defined above,
from 10 to 99.5 wt % of an aqueous medium with neutral or acid pH.

Advantageously, the composition comprises:
from 0.5 to 60 wt % of powder according to the invention, and
from 40 to 99.5 wt % of an aqueous medium with neutral or acid pH, preferably with pH in the range from 1 to 7, preferably from 4 to 6.5. Preferably, the aqueous medium is water and said composition forms a stable aqueous dispersion without surfactant.

The aqueous dispersion according to the invention has the form of a macroscopically homogeneous dispersion, having a milky appearance of varying thickness depending on the concentration of polyamide in the dispersion, but always homogeneous. The expression "homogeneous fluid composition" signifies that the powder and the aqueous medium cannot be distinguished with the naked eye after stirring. If the composition is homogeneous, only a liquid can be observed.

These properties of the aqueous dispersions of powder according to the invention are confirmed, even at high concentrations of polyamide, for example from 60 to 70 wt % of polyamide relative to the total weight of the dispersion, even in the absence of surfactant.

The powders and aqueous dispersions of the present invention are particularly suitable for certain applications, notably textiles and composites, for which working at acid pH is preferred, which guarantees better adherence of the polyamide on the textile.

The aqueous dispersions of the present invention are also suitable for formulation of cosmetics that require a neutral or acid pH, suitable for the skin, preferably in the pH range from 5.5 to 6.5.

Thanks to the polyamide powder according to the invention, the formulator no longer needs to adapt beforehand the form of the polyamides sold commercially in the form of powder or granules, to be able to incorporate them in water.

Preferably, said aqueous medium with neutral or acid pH comprises water, of which at most 10%, preferably at most 5%, preferably at most 2%, preferably 0%, may be replaced with thickeners. Any type of thickener commonly used by formulators may be used. The thickener slows the downward movement of the dispersed polyamide particles under the effect of gravity. It therefore prevents sedimentation of the particles. For example, the thickeners of an aqueous continuous phase, notably in the cosmetics area, are substances generally of vegetable origin: extracts from algae (alginates) or from seeds (galactomannans, pectins), but also synthetic (carbomer=Carbopol).

The present invention also relates to a method of manufacturing polyamide powder according to the invention, comprising the following steps:

A—Stir a mixture of polyamide, water, and phosphorus-based Brønsted acid (acid P) preferably comprising phosphoric acid ($H_3PO_4$), to form an emulsion, in the following conditions:
said starting polyamide comprises more than 50 mol % of amine ends among the total number of amine and acid ends of the polyamide,
the molar ratio [acid P]/[amine ends] is in the range from 0.1 to less than 5, preferably between 0.25 and 5, preferably in the range from 0.5 to 3, preferably from 2 to 3,
the amount of polyamide by weight relative to the total weight of the mixture represents from 0.5 to 60%, preferably from 10 to 50%, preferably from 20 to 50%, or better still from 30 to 40%,
the temperature of the mixture is above the melting point of the polyamide;
the stirring speed and stirring time are sufficient to form a stable homogeneous mixture, i.e. an emulsion of molten polyamide droplets with D50 in the range from 100 nm to 50 µm dispersed in water, then B—Cool the emulsion obtained in step A, with stirring, to room temperature (i.e. a temperature that may be in the range from 5 to 50° C.), so that an aqueous dispersion of polyamide particles according to the invention is obtained.

If all the conditions of step A are respected, stirring leads to the emulsion of molten polyamide and then a stable dispersion. Otherwise, despite stirring, an emulsion is not obtained, being outside of these conditions.

In step A, the molar ratio [acid P]/[amine ends] is generally in the range from 0.1 to less than 5. However, the following preferences should be noted:
the molar ratio [acid P]/[amine ends] is preferably between 0.25 and 5 especially in the case when said polyamide contains less than 100 µEq/g of amine ends, as is the case in tests 2 to 5 of example 1 of the present invention; and
the molar ratio [acid P]/[amine ends] is preferably below these values, and may be in the wider range from 0.1 (inclusive) to less than 5 (5 excluded), in the case when said polyamide contains at least 100 µEq of amine ends per gram of polyamide as is the case in the tests in example 2 of the present invention.

The form of the starting polyamide is of no importance in step A, since it is molten during mixing. Consequently, any form may be envisaged for the starting polyamide. To reduce the time for melting and mixing, the starting polyamide is preferably in finely divided form, regardless of its particle size, generally between 60 µm and some millimeters, notably in the form of granules, powder, fiber, or other forms.

Preferably, the polyamide is incorporated according to the method of the invention, with stirring in the range from 100 to 5000 revolutions per minute, preferably from 1000 rev/min to 2000 rev/min, preferably from 500 rev/min to 1500 rev/min. For example, a blade, propeller or disk stirrer or turbine is used, for example of Rushton® make or equivalent. Preferably the stirring speed is in the range from 100 to 5000 rev/min and the stirring time in the range from 5 minutes to 1 hour, preferably in the range from 10 to 30 minutes.

Advantageously, the method of the invention further comprises a step:
C—Recover the polyamide particles, notably by separation, filtration and/or drying, evaporation, spray drying, from the aqueous dispersion obtained in step B.

Advantageously, the method of the invention further comprises a step:

D—Re-disperse the PA particles in a neutral or acid aqueous medium, so that a dispersion is obtained comprising from 0.5 to 90%, preferably from 0.5 to 70%, by weight of PA particles.

The present invention also relates to the use of a powder or of a composition according to the invention in all the applications simultaneously requiring properties of narrow granulometric distribution in the case of powders, properties of fine, homogeneous dispersions, film-forming properties, properties of adhesion, compatibility and affinity with matrixes, in particular polar matrixes. Among the applications of the powders and dispersions according to the invention, we may mention for example can coating, release paper, gluing, fabric covering, surface coating, coating of wires, fibers, filaments, coils, manufacture of films, fine gluing, inks and paints, size, textile treatments, fabric covering, treatment of paper, lubricants, hot melt adhesives (HMA).

The present invention also relates to the use of a polyamide powder according to the invention for manufacturing a cosmetic, pharmaceutical or perfumery product, said polyamide being incorporated directly in the formulation in the form of a powder or of a composition according to the invention.

The present invention notably relates to a composition according to the invention as defined above, said composition being a colored, noncolored and/or transparent product selected from the following products:

makeup products for the human face and body, such as foundation, tinted cream, loose or compacted powder, eye shadow, mascara, eye liner, lipstick, nail varnish;

care products for the human face and body, such as cream, milk, lotion, mask, peeling product, cleansing and/or makeup removal products, deodorants, antiperspirants, shaving products, hair removal products;

hair products, such as shampoos, hair shaping products, styling products, antidandruff products, products against hair loss, products against dryness of the hair, hair coloring products, bleaching products;

perfumery products, such as perfume, milk, cream, loose or compacted perfumed powder.

EXAMPLES

The following examples illustrate the present invention without limiting its scope. Unless stated otherwise, all the percentages are by weight.

COPAs Used:

COPA1: copolyamide 6/6.6/12, compound of caprolactam, hexamethylenediamine, adipic acid, lauryllactam, diethylenetriamine, undecylenic acid, with m.p. 125° C., containing 25 μeq/g of acid chain ends, 63 μeq/g of amine chain ends and 120 μeq/g of alkyl chain ends.

COPA2: copolyamide 6/6.6/12, compound of caprolactam, hexamethylenediamine, adipic acid, lauryllactam, m.p.=125° C. containing 23 μeq/g of acid chain ends and 319 μeq/g of amine chain ends.

Example 1

Six tests (tests 1 to 6) of aqueous dispersions of COPA1 with molar ratio $H_3PO_4/NH_2$ chain ends=0.25/0.5/1/2/3 and 5 were carried out.

Granules of COPA1, deionized water (so as to have a 30% dry extract) and phosphoric acid are put in an autoclave with a 1 L glass tank, equipped with a stirrer of the double propeller type with 6 inclined blades. The tank has an inside diameter of 100 mm and is heated by circulation of oil in a double jacket. The stirrer has a diameter of 50 mm. The medium is inerted with nitrogen and heated to 150° C. matter with stirring at 1000 revolutions per minute (rpm). This temperature is maintained for 30 min and then the medium is cooled to 50° C. An aqueous dispersion of fine polyamide particles is thus obtained in tests 2 to 5, and the size distribution of the particles is measured by laser diffraction.

Summary of the operating conditions: Heating phase at 1000 rev/min, plateau 30 min, 150° C., 1000 rev/min, then cooling.

TABLE 1

| Test No. | Molar ratio $H_3PO_4$/amine chain ends | D50 (μm) | Remarks |
| --- | --- | --- | --- |
| 1 comparative | 0.25 | | Dispersion unstable/aggregation |
| 2 invention | 0.5 | 19.3 | Stable dispersion |
| 3 invention | 1 | 1.1 | Stable dispersion |
| 4 invention | 2 | 2.1 | Stable dispersion |
| 5 invention | 3 | 2.1 | Stable dispersion |
| 6 comparative | 5 | | Formation of foam/Dispersion unstable |

Table 1 shows that tests 2 to 5 according to the invention allow a stable aqueous dispersion of polyamide to be obtained when the proportion of phosphoric acid conforms to the invention. In test 1, the $H_3PO_4$ content is too low to stabilize the particles and form a dispersion, whereas in test 6 the content is too high and considerable foaming is observed, without the possibility of obtaining particles or a stable dispersion.

The dispersions obtained with a 30% dry extract in tests 2 to 5 may then be filtered and then redispersed in water using a mixer. It is possible to obtain dry extracts above 30%, and formulate easily using these dispersions.

Increasing the Dry Extract: Test 3.2 According to the Invention:

In these tests, the dry extract of the dispersions obtained is increased.

For this, firstly, filtration is carried out on a No. 4 frit from test 3 (molar ratio=1) to obtain a moist powder. This powder is then redispersed in water with a mixer; it is thus possible to increase the dry extract and obtain a texture of viscous homogeneous paste. It is then observed with the laser granulometer that this manipulation has no effect on the granulometry of the particles.

Conclusions from the Tests in Example 1

The dispersions prepared with molar ratios of 0.5; 1; 2 and 3 are preferred as they have interesting properties, namely particles of the order of a micron, with D50 in the range from 1 to 15 μm. Moreover, the dispersions with molar ratio $H_3PO_4/NH_2$=2 and 3 respectively display a particularly stable and homogeneous state, and they may easily be redispersed and/or concentrated.

Observations with the laser granulometer: The solutions with molar ratio $H_3PO_4/NH_2$=0.5/1/2 and 3 were analyzed with the laser granulometer. Two samples were analyzed for each ratio. The results obtained for granulometric distribution (by volume) are shown in the following Table 2:

TABLE 2

| | Test | | | |
|---|---|---|---|---|
| | Test 2 | Test 3 | Test 4 | Test 5 |
| | | D50 (µm) | | |
| % below | 19.370 Size µm | 1.129 Size µm | 2.119 Size µm | 2.126 Size µm |
| 10 | 4.2145 | 0.278 | 0.308 | 1.2965 |
| 25 | 10.92 | 0.514 | 1.411 | 1.668 |
| 50 | 19.370 | 1.129 | 2.119 | 2.126 |
| 75 | 25.700 | 1.731 | 3.149 | 2.865 |
| 90 | 31.295 | 2.064 | 4.127 | 3.763 |

Example 2: Tests 7 and 8 According to the Invention

COPA2 is dispersed according to the same procedure as in example 1.

Ratio $H_3PO_4/NH_2$ chain ends=0.1

Stirring speed: 1000 rev/min for test 7; 1300 rev/min for test 8.

The dispersion obtained is white and opaque in both tests, with pH 6-7.

In test 7, the final dry extract is 31.54%, and D50=5.39 µm.

In test 8, the final dry extract is 32.60%, and D50=2.95 µm.

These tests in example 2 illustrate the case when the $H_3PO_4$/amine ends ratio may be less than or equal to 0.25, and may be in the wider range from 0.1 to 5 when said polyamide contains at least 100 µEq/g of amine ends.

It may be noted that with increase in the molar percentage of amine ends among the total number of amine and acid ends of the polyamide, the amount of phosphoric acid required for neutralizing and dispersing the polyamide decreases. Phosphoric acid neutralizes several $NH_2$ ends of different polyamide particles at the same time. By a steric effect, phosphoric acid prevents the particles with $NH_2$ ends from coagulating with one another, and keeps the particles dispersed in the water.

Example 3: Comparative Tests 9 to 11

Three tests are carried out according to the same procedure and the same operating conditions as in example 1, except that phosphoric acid is replaced with a "comparative acid" different from a phosphorus-containing Brønsted acid. The comparative acid is heptanoic acid in test 9, methanesulfonic acid in test 10, and sulfuric acid in test 11.

In these tests 9 to 11, the ratio [comparative acid]/[$NH_2$ chain ends]=1.

At the end of this procedure, in each test 9 to 11 a block of polyamide is obtained, not a dispersion of fine polyamide particles.

Example 4

Use of a powder of polyamide 10.10 with D50 equal to 20 µm, obtained by the method described in the patent, for manufacturing composites.

Production of epoxy-based composite resins: TGMDA/DDS/DDA: systems with high Tg.

Epoxy: TGMDA: N,N,N',N-tetraglycidyl 4,4'-diaminodiphenylmethane (Araldite MY 720, Huntsman)

Crosslinking agent: DDS/DDA: 4,4'-diaminodiphenylsulfone (HT 976, Huntsman)/dicyandiamide Catalyst: 3-3,4-dichlorophenyl)-1,1-dimethylurea (diuron)

Composition of the resins: 1 epoxy group to 0.85 amine hydrogen of DDS/DDA; DDA/DDS ratio: 0.25; diuron/DDS ratio: 0.01. Three different contents of powder PA10.10 in the resin are tested: 0 phr, 10 phr, 20 phr, where phr denotes "parts per hundred of resin, by weight". Crosslinking cycle: 1 h at 110° C., 1 h at 120° C., 1 h at 130° C., 1 h at 140° C., 1 h at 150° C., 1 h at 180° C.

The critical stress intensity factor K1C is measured (standard ASTMD5045, in MPa/$\sqrt{m}$; it defines, for the material, the critical value of stress beyond which rupture occurs):

| Powder content (phr) | K1C |
|---|---|
| 0 | 0.65 |
| 10 | 0.7 |
| 20 | 0.8 |

The use of powder according to the invention improves and endows excellent breaking strength on the epoxy resin.

The invention claimed is:

1. A water-dispersible powder based on polyamide particles, wherein
    said polyamide comprises at least one copolyamide;
    said polyamide comprises more than 50 mol % of amine ends among the total number of amine and acid ends of the polyamide;
    said particles bear, on their surface, primary amine groups at least partially neutralized by a phosphorus-based Brønsted acid (acid P) at a molar ratio [acid P]/[amine ends] in the range from greater than 0.25 to less than 5; and
    D50 of the particles is in a range from 100 nm to 50 µm.

2. The powder as claimed in claim 1, wherein the powder is directly dispersible in an aqueous medium with neutral or acid pH.

3. The powder as claimed in claim 1, in which the polyamide comprises at least one of the following monomers: 4.6, 4.T, 5.6, 5.9, 5.10, 5.12, 5.13, 5.14, 5.16, 5.18, 5.36, 6, 6.6, 6.9, 6.10, 6.12, 6.13, 6.14, 6.16, 6.18, 6.36, 6.T, 9, 10.6, 10.9, 10.10, 10.12, 10.13, 10.14, 10.16, 10.18, 10.36, 10.T, 11, 12, 12.6, 12.9, 12.10, 12.12, 12.13, 12.14, 12.16, 12.18, 12.36, 12.T, and mixtures thereof.

4. The powder as claimed in claim 1, in which the polyamide comprises at least one copolyamide selected from: PA 6/6.6/12, PA 6/6.6/11/12, PA 6/12, PA 6.9/12, PA Pip.9/Pip.12/11, PA 6/IPD.6/12, PA IPD.9/12, PA6/MPMD.12/12, PA 6/6.12/12, PA 6/Pip.12/12, PA 6/6.6/6.10/6.1, PA 6.10/Pip.10/Pip.12, PA 6/11/12, PA Pip.12/12, PA IPD.10/12, PA Pip.10/12, PA 6/11, PA Pip.10/11/Pip.9, PA 6/6.6/6.10, and mixtures thereof.

5. The powder as claimed in claim 1, wherein the powder contains particles of spheroidal shape and with a porous surface.

6. A homogeneous fluid composition comprising:
    from 0.5 to 90 wt % of powder as claimed in claim 1,
    from 10 to 99.5 wt % of an aqueous medium with neutral or acid pH.

7. The composition as claimed in claim 6, wherein the composition comprises:
    from 0.5 to 60 wt % of the powder, and
    from 40 to 99.5 wt % of an aqueous medium with neutral or acid pH, said composition forming a stable aqueous dispersion without surfactant.

8. The composition as claimed in claim 6, in which said aqueous medium with neutral or acid pH comprises water, of which at most 10% may be replaced with thickeners.

9. A method of manufacturing the polyamide powder as claimed in claim 1, comprising:
- A—stirring a mixture of polyamide, water, and phosphorus-based Brønsted acid (acid P) to form an emulsion, in the following conditions:
  said polyamide comprises at least one copolyamide;
  said starting polyamide comprises more than 50 mol % of amine ends among the total number of amine and acid ends of the polyamide;
  the molar ratio [acid P]/[amine ends] is in the range from greater than 0.25 to less than 5;
  the amount of polyamide by weight relative to the total weight of the mixture represents from 0.5 to 60%,
  the temperature of the mixture is above the melting point of the polyamide;
  the stirring speed and stirring time are sufficient, the stirring speed being in the range from 100 to 5000 rev/min and the stirring time being in the range from 5 minutes to 1 hour, to form a stable homogeneous mixture;
- B—cooling the emulsion obtained in step A with stirring so that an aqueous dispersion of polyamide particles is obtained; and
- C—recovering the polyamide particles from the aqueous dispersion obtained in step B, wherein
  said polyamide comprises more than 50 mol % of amine ends among the total number of amine and acid ends of the polyamide;
  said particles bear, on their surface, primary amine groups at least partially neutralized by the phosphorus-based Brønsted acid; and
  D50 of the particles is in a range from 100 nm to 50 µm.

10. The method as claimed in claim 9, further comprising a step:
- D—re-dispersing the polyamide particles in a neutral or acid aqueous medium, so that a dispersion is obtained comprising from 0.5 to 90%, by weight of polyamide particles.

11. The powder as claimed in claim 1, wherein the powder is used in can coating, release paper, glue, fabric covering, surface coating, wire coating, fibers, filaments, coils, manufacture of films, fine glue, inks, paints, textile treatments, paper treatment, lubricants, hot melt adhesives (HMA), or composites.

12. The powder as claimed in claim 1, wherein the powder is used in manufacturing a cosmetic, pharmaceutical or perfumery product.

13. The powder as claimed in claim 1, wherein a core of the particles contains at least one cosmetic, pharmaceutical or perfumery product.

14. The composition as claimed in claim 6, said composition being a colored, noncolored and/or transparent product selected from the following products:
  makeup products for the human face and body;
  care products for the human face and body;
  hair products;
  perfumery products.

15. The powder as claimed in claim 1, wherein:
  the molar ratio [acid P]/[amine ends] is in the range from 0.5 to 3.

* * * * *